United States Patent [19]

Nozulak et al.

[11] Patent Number: 5,190,941
[45] Date of Patent: Mar. 2, 1993

[54] USE OF NAPHTHOXAZINES FOR THE TREATMENT OF CONDITIONS ASSOCIATED WITH CEREBRAL ISCHAEMIA

[75] Inventors: Joachim Nozulak, Heitersheim, Fed. Rep. of Germany; André Sauter, Bottmingen, Switzerland; Jean-Marie Vigouret, Alle, Switzerland

[73] Assignee: Sandoz Ltd., Basel, Switzerland

[21] Appl. No.: 626,352

[22] Filed: Dec. 12, 1990

[30] Foreign Application Priority Data

Dec. 14, 1989 [GB] United Kingdom ............... 8928316
Feb. 3, 1990 [DE] Fed. Rep. of Germany ....... 4003262

[51] Int. Cl.[5] ............... A61K 31/535; C07D 265/34
[52] U.S. Cl. .................................. 514/229.8; 544/101
[58] Field of Search .................. 514/229.8, 231.2; 544/155, 101

[56] References Cited

U.S. PATENT DOCUMENTS 4,540,691 4/1984 Horn .................................. 514/211
4,656,167 4/1987 Nozulak et al. ..................... 514/227

FOREIGN PATENT DOCUMENTS 0233728 8/1987 European Pat. Off. .

OTHER PUBLICATIONS

*Chemical Abstracts* 108(5): 37848g, 1988, Meguro & Nishikawa, Preparation of 2-[4-Phenyl-1-Piperazinyl-)alkyl]-2H-1,4-Benzoxazin-3(4H)-Ones as Calcium Channel Blockers.

*Primary Examiner*—Frederick E. Waddell
*Assistant Examiner*—Kimberly R. Jordan
*Attorney, Agent, or Firm*—Gerald D. Sharkin; Robert S. Honor; Thomas O. McGovern

[57] ABSTRACT

Compounds of formula I

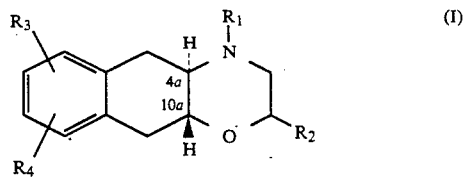

wherein $R_1$, $R_2$, $R_3$ and $R_4$ are as defined in the description, are useful for the treatment of conditions associated with cerebral ischaemia, e.g. stroke.

8 Claims, No Drawings

USE OF NAPHTHOXAZINES FOR THE TREATMENT OF CONDITIONS ASSOCIATED WITH CEREBRAL ISCHAEMIA

The present invention relates to a new pharmaceutical use of 3,4,4a,5,10,10a-hexahydro-2H-naphth[2,3-b]-1,4-oxazines.

More particularly the present invention relates to a new pharmaceutical use for compounds of formula I

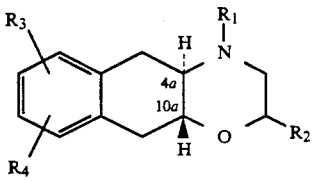

wherein
$R_1$ and $R_2$ independently are hydrogen or $(C_{1-4})$alkyl,
$R_3$ is hydroxy or $(C_{1-4})$alkoxy and
$R_4$ is $(C_{1-4})$alkylthio, $(C_{1-4})$alkylsulfoxide, $(C_{1-4})$alkylsulfone, chlorine, bromine, iodine or trifluoromethyl,
in free base or pharmaceutically acceptable acid addition salt form, hereinafter referred to as compounds for use according to the invention.

The compounds of formula I have the trans configuration in positions 4a and 10a. Following accepted nomenclature conventions, the above representation of formula I embraces the trans isomers with the configuration IA as well as those with the configuration IB.

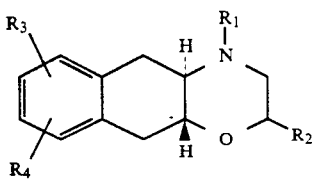

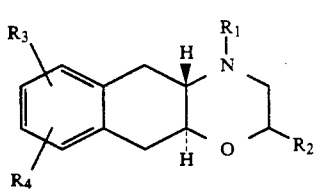

The formula I covers both the racemates and the optically active forms.

In the case where $R_2$ is not hydrogen, again both possible isomers as well as the corresponding racemates are covered.

The compounds for use according to the invention as well as a process for their production are known e.g. from U.S. Pat. No. 4,656,167. This patent also discloses the use of the compounds for stimulating the central nervous system, e.g. for increasing vigilance, and for treating depressions.

In accordance with the present invention it has now been surprisingly found that the compounds for use according to the invention are useful in the prophylaxis and therapy of conditions associated with cerebral ischaemia, e.g. stroke.

This utility of said compounds is indicated by animal tests, e.g. by the reduction of mortality in the middle cerebral artery (MCA) occlusion model in rats at a dosage of 1-30 mg/kg/day p.o. [cf. A. Tamura et al., J. Cereb. Blood Flow Metabol. 1, 53-60 (1981), A. Sauter, M. Rudin, Stroke 17, 1228-1234 (1986)]. The compounds are administered orally each day from the third day after MCA occlusion, during 3 weeks. For example with the (−)-(4aR,10aR)-3,4,4a,5,10,10a-hexahydro-6-methoxy-4-methyl-9-methylthio-2H-naphth[2,3-b]-1,4-oxazine, a marked increase of the number of surviving animals is observed after treatment with 3 mg/kg/day p.o.

The compounds for use according to the invention are therefore useful in the prophylaxis and therapy of conditions associated with cerebral ischaemia, e.g. stroke.

For this indication the appropriate dosage will of course vary depending upon, for example, the compound employed, the host, the mode of administration and the nature and severity of the condition being treated. However, in general, satisfactory results in animals are indicated to be obtained at a daily dosage of from about 3 to about 30 mg/kg animal body weight. In larger mammals, for example humans, an indicated daily dosage is in the range from about 1 to about 200 mg of a compound according to the invention conveniently administered, for example, in divided doses up to four times a day.

The compounds for use according to the invention may be administered by any conventional route, in particular enterally, preferably orally, e.g. in the form of tablets or capsules, or parenterally, e.g. in the form of injectable solutions or suspensions.

The compounds for use according to the invention may be administered in free base form or in pharmaceutically acceptable acid addition salt form e.g. the hydrogenmalonate. Such salts exhibit the same order of activity as the free base.

The present invention also provides pharmaceutical compositions comprising the compounds according to the invention in association with at least one pharmaceutical carrier or diluent for use in the treatment of conditions associated with cerebral ischaemia. Such compositions may be manufactured in conventional manner. Unit dosage forms may contain for example from about 0.3 mg to about 100 mg of the compound in free base or pharmaceutically acceptable acid addition salt form.

Capsules containing the ingredients indicated below may be prepared by conventional techniques and are administered at a dose of e.g. one to two capsules up to 3 times a day.

| INGREDIENTS | WEIGHT (mg) |
| --- | --- |
| (−)-(4aR,10aR)-3,4,4a,5,10,10a-hexahydro-6-methoxy-4-methyl-9-methylthio-2H-naphth[2,3-b]-1,4-oxazine hydrogenmalonate | 4.12 |
| Silica, colloidal anhydrous | 1.80 |
| Magnesium stearate | 3.60 |
| Maize starch | 72.00 |
| Lactose | 278.48 |
| Contents | 360.00 |

The invention further provides the use of a compound of formula I in free base or pharmaceutically acceptable acid addition salt form for the manufacture of a pharmaceutical composition for treating conditions associated with cerebral ischaemia.

The invention furthermore provides a method for the treatment of conditions associated with cerebral ischaemia in a subject in need of such treatment, which comprises administering to said subject a therapeutically effective amount of a compound of formula I in free base or pharmaceutically acceptable acid addition salt form.

The invention also provides the (−)-(4aR,10aR)-3,4,4a,5,10,10a-hexahydro-6-methoxy-4-methyl-9-methylthio-2H-naphth[2,3-b]-1,4-oxazine in form of its hydrogen malonate. The compound in free base form and in form of its hydrochloride are disclosed in the above mentioned U.S. Pat. No. 4,656,167. According to Example 2, the free base is obtained as an oil. The hydrochloride as well as various other salts prepared by the applicant, including the hydrogen maleinate and the hydrogen fumarate, present the disadvantage of showing polymorphism. It is known, for instance, that polymorphous salts upon p.o. administration cause non-homogenous resorption.

It has now surprisingly been found that the (−)-(4aR,10aR)-3,4,4a,5,10,10a-hexahydro-6-methoxy-4-methyl-9-methylthio-2H-naphth[2,3-b]-1,4-oxazine in form of its hydrogen malonate, hereinafter referred to as compound according to the invention, does not show polymorphism.

The compound according to the invention has never been specifically disclosed in literature. It may be prepared from the free base by reaction with malonic acid, e.g. as described in the following example.

The compound according to the invention possesses central, noradrenergic activity which was demonstrated as indicated in the above mentioned U.S. Pat. No. 4,656,167. It is therefore useful as psychostimulant and as antidepressant. Moreover according to the present invention it is useful in the prophylaxis and therapy of conditions associated with cerebral ischaemia, e.g. stroke.

The appropriate dosage and administration routes are as disclosed for the 3,4,4a,5,10,10a-hexahydro-2H-naphth[2,3-b]-1,4-oxazines of the above mentioned U.S. Pat. No. 4,656,167 for the psychostimulant and antidepressant uses and for the compounds of formula I of the present invention for the anti-ischaemic use.

The invention further provides a pharmaceutical composition which incorporates as active agent the compound according to the invention, in association with a pharmaceutical carrier or diluent.

In the following example, all temperatures are uncorrected and are in degrees Centigrade.

EXAMPLE (−)-(4aR,10aR)-3,4,4a,5,10,10a-hexahydro-6-methoxy-4-methyl-9-methylthio-2H-naphth[2,3-b]-1,4-oxazin hydrogen malonate A solution of 0.75 g (7.2 mmol) of malonic acid in acetone is added to 2.00 g (7.2 mmol) of (−)-(4aR,10aR)-3,4,4a,5,10,10a-hexahydro-6-methoxy-4-methyl-9-methylthio-2H-naphth[2,3-b]-1,4-oxazine in acetone. The crystallisation product is filtered off by suction, washed with ethyl acetate and ether and dried. After recrystallisation from acetone/ethyl acetate/ether, the compound of the title is obtained.

Mp=127°; $[\alpha]_D^{20} = -102.5°$ (c=0.5 in methylene chloride: methanol, 1:1).

What we claim is:

1. The (−)-(4aR,10aR)-3,4,4a,5,10,10a-hexahydro-6-methoxy-4-methyl-9-methylthio-2H-naphth[2,3-b]-1,4-oxazine hydrogen malonate.

2. A pharmaceutical composition comprising a therapeutically effective amount of (−)-(4aR,10aR)-3,4,4a,5,10,10a-hexahydro-6-methoxy-4-methyl-9-methylthio-2H-naphth[2,3-b]-1,4-oxazine hydrogen malonate and a pharmaceutically acceptable carrier or diluent.

3. A method of treating cerebral ischaemia in a subject in need of said treatment, which comprises administering to said subject a therapeutically effective amount of a compound of the formula I

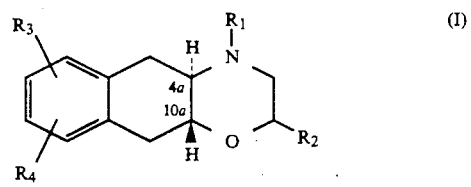

wherein
$R_1$ and $R_2$ are each independently hydrogen or ($C_{1-4}$)alkyl,
$R_3$ is hydroxy or ($C_{1-4}$)alkoxy and
$R_4$ is ($C_{1-4}$)alkylthio, ($C_{1-4}$)alkylsulfoxide, ($C_{1-4}$)alkylsulfone, chlorine, bromine, iodine, or triflouromethyl, in free base form or pharmaceutically acceptable acid addition salt form.

4. A method according to claim 3 of treating stroke.

5. A method according to claim 3 or 4 in which the compound is (−)-(4aR,10aR)-3,4,4a,5,10,10a-hexahydro-6-methoxy-4-methyl-9-methylthio-2H-naphth[2,3-b]-1,4-oxazine in free base form or pharmaceutically acceptable acid addition salt form.

6. A method according to claim 3 or 4 in which the compound is (−)-(4aR,10aR)-3,4,4a,5,10,10a-hexahydro-6-methoxy-4-methyl-9-methylthio-2H-naphth[2,3-b]-1,4-oxazine hydrogen malonate.

7. A method according to claim 3 or 4 in which the compound is administered in a daily dose of from about 1 to about 200 mg.

8. A method according to claim 3 or 4 in which the compound is administered in a unit dose of from about 0.3 to about 100 mg.

* * * * *